(12) United States Patent
Loupas et al.

(10) Patent No.: US 12,213,838 B2
(45) Date of Patent: Feb. 4, 2025

(54) TEMPORALLY BALANCED MULTI-MODE MASTER IMAGING SEQUENCE FOR ULTRASONIC CONTRAST IMAGING

(71) Applicant: KONINKLIJKE PHILIPS N.V., Eindhoven (NL)

(72) Inventors: Thanasis Loupas, Kirkland, WA (US); Paul Sheeran, Woodinville, WA (US); Charles Tremblay-Darveau, Seattle, WA (US); Jeffry Earl Powers, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 206 days.

(21) Appl. No.: 17/617,360

(22) PCT Filed: Jun. 4, 2020

(86) PCT No.: PCT/EP2020/065504
§ 371 (c)(1),
(2) Date: Dec. 8, 2021

(87) PCT Pub. No.: WO2020/249464
PCT Pub. Date: Dec. 17, 2020

(65) Prior Publication Data
US 2022/0218312 A1 Jul. 14, 2022

Related U.S. Application Data

(60) Provisional application No. 62/859,936, filed on Jun. 11, 2019.

(51) Int. Cl.
*A61B 8/08* (2006.01)
*A61B 8/00* (2006.01)
(Continued)

(52) U.S. Cl.
CPC .............. *A61B 8/5276* (2013.01); *A61B 8/06* (2013.01); *A61B 8/14* (2013.01); *A61B 8/463* (2013.01);
(Continued)

(58) Field of Classification Search
None
See application file for complete search history.

(56) References Cited

U.S. PATENT DOCUMENTS

| 2004/0087858 | A1* | 5/2004 | Hao | G01S 15/8963 |
| | | | | 600/458 |
| 2005/0124895 | A1* | 6/2005 | Jensen | G01S 7/52039 |
| | | | | 600/453 |

(Continued)

FOREIGN PATENT DOCUMENTS

WO 2019023422 A1 1/2019

OTHER PUBLICATIONS

International Search Report and Written Opinion for PCT/EP2020/065504; Mailing date: Sep. 1, 2020; 13 pages.
(Continued)

*Primary Examiner* — Joel Lamprecht
*Assistant Examiner* — Nyrobi Celestine (57) ABSTRACT

A particular sequence of ultrasound transmissions and corresponding echo receptions enables the production of Amplitude Modulated (AM) and Amplitude Modulated Phase Inverted (AMPI) signals that are temporally balanced. Temporal balancing significantly reduces tissue artifacts caused by movement of tissue during acquisition of the ultrasound echoes. Additionally, in combining the selected echo signals to produce the AM5 and AMPI signals, and optionally a Phase Inverted (PI) signal, each of the echo signals is equally weighted to facilitate an amplitude balance (Continued)

that avoids different echoes affecting the produced AM, AMPI, and PI signals differently.

15 Claims, 9 Drawing Sheets

(51) Int. Cl.
    *A61B 8/06*     (2006.01)
    *A61B 8/14*     (2006.01)
    *G01S 7/52*     (2006.01)
    *G01S 15/89*     (2006.01)

(52) U.S. Cl.
    CPC .......... *A61B 8/5207* (2013.01); *G01S 7/5202* (2013.01); *G01S 7/52026* (2013.01); *G01S 7/52039* (2013.01); *G01S 15/8915* (2013.01)

(56) References Cited

U.S. PATENT DOCUMENTS

| | | | |
|---|---|---|---|
| 2005/0256404 A1* | 11/2005 | Sato | G01S 7/52039 600/437 |
| 2006/0036175 A1 | 2/2006 | Guracar et al. | |
| 2008/0200815 A1* | 8/2008 | Van Der Steen | A61B 8/12 600/467 |
| 2008/0228070 A1* | 9/2008 | Phillips | A61B 8/481 600/431 |
| 2013/0137986 A1* | 5/2013 | Takeda | G01S 15/8963 600/447 |
| 2014/0276049 A1* | 9/2014 | Doherty | G01S 7/52042 600/438 |
| 2015/0141830 A1* | 5/2015 | Kakee | A61B 8/5269 600/447 |
| 2016/0151045 A1* | 6/2016 | Pelissier | G01S 7/52046 600/447 |

OTHER PUBLICATIONS

Gong, Ping et al., "Hadamard-Encoded Multipulses for Contrast-Enhanced Ultrasound Imaging", EEE Trans Ultrason Ferroelectrics Freq Control. 2017, vol. 64, No. 11, pp. 1674-1683.

Tremblay-Darveau, Charles et al., "The Role of Microbubble Echo Phase Lag in Multipulse Contrast-Enhanced Ultrasound Imaging", IEEE Trans Ultrason Ferroelectrics Freq Control. 2018 ;vol. 65, No. 8, pp. 1389-1401.

Tremblay-Darveau, Charles et al., "Visualizing the Tumor Microvasculature With a Nonlinear Plane-Wave Doppler Imaging Scheme based on Amplitude Modulation", IEEE Transactions on Medical Imaging, 2016, vol. 35, No. 2, pp. 699-709.

* cited by examiner

TEMPORALLY BALANCED MULTI-MODE MASTER IMAGING SEQUENCE FOR ULTRASONIC CONTRAST IMAGING

CROSS-REFERENCE TO PRIOR APPLICATIONS

This application is the U.S. National Phase application under 35 U.S.C. § 371 of International Application No. PCT/EP2020/065504, filed on Jun. 4, 2020, which claims the benefit of U.S. Provisional Patent Application No. 62/859,936, filed on Jun. 11, 2019. These applications are hereby incorporated by reference herein.

FIELD OF THE INVENTION

This invention relates to the field of contrast-enhanced ultrasound (CEUS) imaging, and in particular to a method and system that employs advanced pulse sequences that combine the advantages of multiple CEUS pulsing schemes.

BACKGROUND OF THE INVENTION

Ultrasound images are created by transmitting ultrasonic pulses at varying amplitudes and frequencies, receiving the echoes corresponding to each transmitted pulse, and processing the echoes to create the image. Often, an ultrasonic contrast medium is injected in a blood vessel of the subject to enhance viewing of blood flow through the blood vessels and perfused tissue. The ultrasonic contrast medium typically contains microbubbles that substantially increase the strength of signals emanating from blood and, therefore, preferentially enhance those signals vs signals received from tissue not perfused by blood.

However, ultrasound signals that provide a strong acoustic pressure can destroy the microbubbles in the blood vessels. Accordingly, the amplitude of the ultrasound signal is controlled to remain below a given limit to minimize microbubble destruction; correspondingly, the amplitude of the microbubble echoes is fairly small. Consequently, these low-amplitude microbubble echoes are often obscured by the larger echoes from the surrounding tissues.

Recognizing the benefits to be gained by enabling an ultrasound image to display blood flow in vessels as well as tissue perfusion, techniques have been developed to distinguish microbubble echoes from non-perfused tissue echoes based on the characteristics of the echoes. Tissue echoes generally exhibit a linear response, whereas microbubble echoes exhibit a primarily nonlinear response, and distinguishing microbubble echoes from tissue echoes is conventionally accomplished by canceling linear signals ('tissue cancelation') in the received echo signals.

Three techniques (or sub-modes) are commonly available for tissue cancelation: pulse inversion (PI), amplitude modulation (AM), and amplitude modulation pulse inversion (AMPI). In conventional contrast imaging ultrasound systems, each of the three sub-modes PI, AM, and AMPI, individually or in combination are used to create ultrasound images because each of these sub-modes has its own set of advantages and disadvantages with respect to resolution, bubble sensitivity, penetration, artifacts, and so on.

USPA 2005/0256404 discloses sequences of two pulses that can provide each of the PI, AM, and AMPI signals, and is incorporated by reference herein.

Figure 1A:
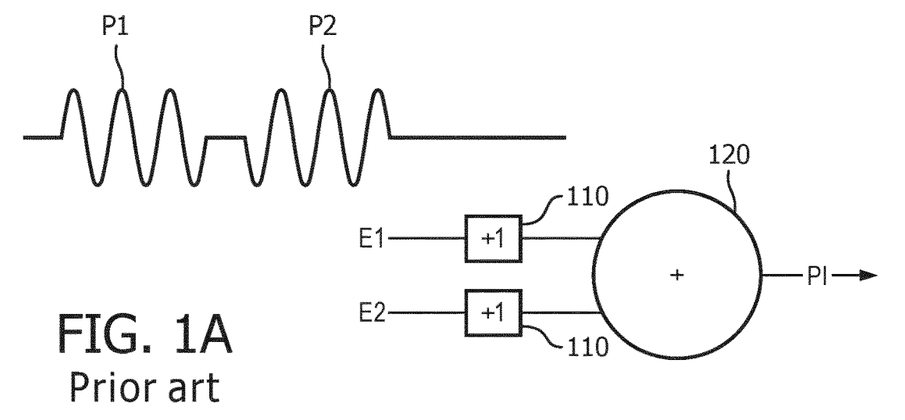
FIGS. 1A-1D illustrate the transmission and reception of ultrasound pulses to produce PI, AM, and AMPI signals.

Pulse Inversion (PI) is illustrated in FIG. 1A. Two pulses P1, P2 are transmitted, each at an opposite phase. The received echo signals E1, E2, are provided to a unity (+1) gain amplifier 110 and combined at adder 120. At the adder 120, the opposing-phase signals cancel each other, removing the linear components of the signal due to non-perfused tissue echoes. The remainder signal PI is representative of the nonlinear components due to contrast microbubble echoes from blood vessels and blood-perfused tissue.

Figure 1B:
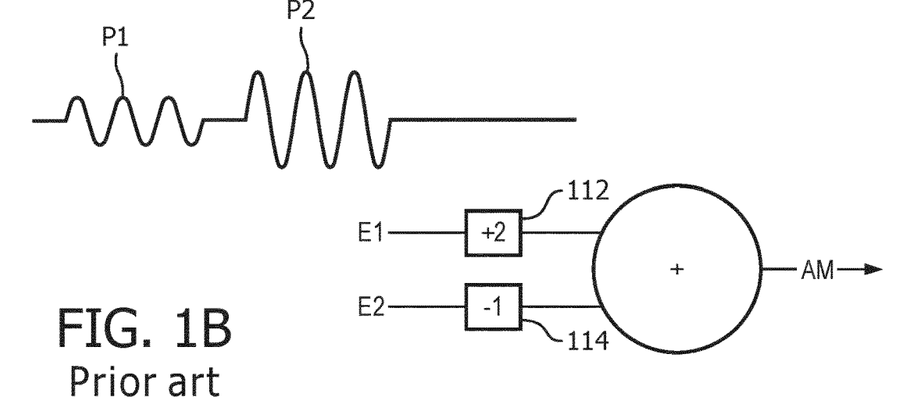

Amplitude Modulation (AM) is illustrated in FIG. 1B. Two pulses are transmitted, one pulse P1 at half amplitude, and one pulse P2 at full amplitude, each at the same phase. The half amplitude echo E1 is doubled via the +2 gain amplifier 112, while the full amplitude echo E2 is inverted at the negative (−1) unity gain amplifier 114. When these signals are summed 120, the resulting amplitude of the linear signals is zero, and the remainder signal AM is another representation of the nonlinear components (microbubble echoes).

Figure 1C:
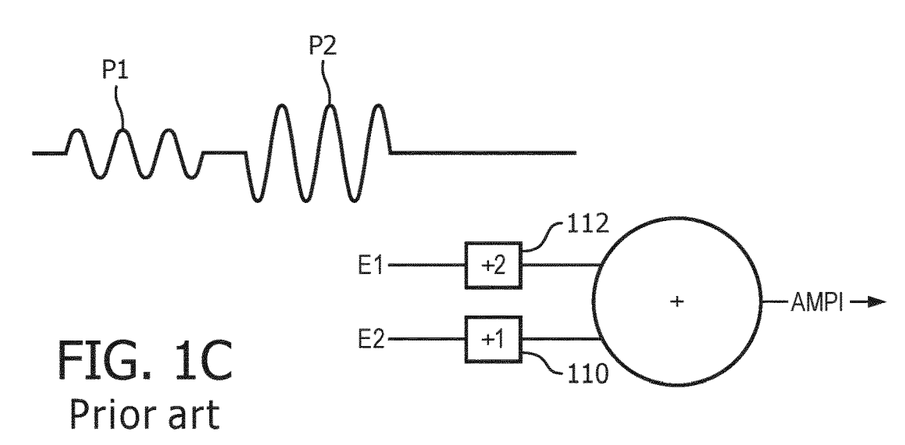

Amplitude Modulation Pulse Inversion (AMPI), illustrated in FIG. 1C, combines the AM and PI sub-modes, by setting the phase of the full aperture pulse P2 to be opposite the phase of the half aperture pulse P1 in the above AM sequence. In this embodiment, the negative (−1) unity gain amplifier 114 is replaced by a positive (+1) unity gain amplifier 110, and the signals are combined 120. The resulting amplitude of the opposing phase linear signals is zero, and the remaining signal AMPI is another representation of the nonlinear components (microbubble echoes).

Figure 1D:
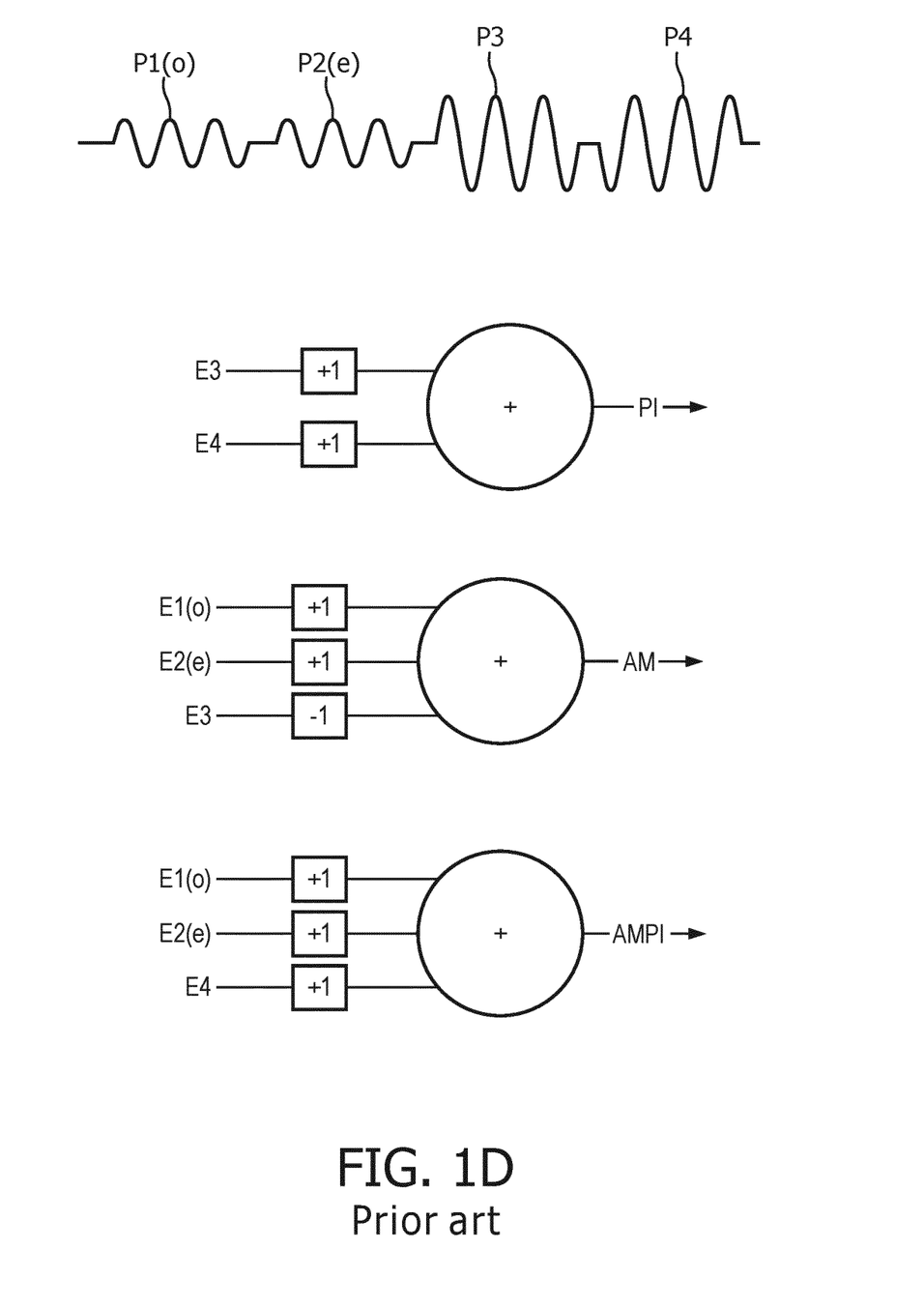

USPA 2005/0256404 also discloses that the half amplitude pulses may be obtained by activating half of the ultrasound transducer elements. The transducer elements may be sequentially numbered, and, in an example embodiment, all of the odd numbered transducer elements are activated to produce half amplitude pulse P1($o$), while all of the even numbered transducer elements are activated to produce half amplitude pulse P2($e$), as illustrated in FIG. 1D. One of skill in the art will recognize that the half amplitude pulses may be obtained in a variety of sequences, such as "enable the first N/2 transducer elements, then the remaining N/2 transmitters"; or, "repeatedly enable every other set of K transducer elements of the N transducer elements, where N/K is an even integer" (e.g. N=18, K=3: set 1={1, 2, 3, 7, 8, 9, 13, 14, 15}; set 2={4, 5, 6, 10, 11, 12, 16, 17, 18}); or, "enable a random set of N/2 transducer elements, then enable the remainder N/2 transducer elements"; etc. For ease of reference and understanding, the terms "odd" (P1($o$)) and "even" (P2($e$)) with respect to pulses of half amplitude are used hereinafter to signify alternate sets of half the transducer elements, regardless of how these sets are selected.

Also illustrated in FIG. 1D are two full amplitude pulses P3 and P4 of opposing phase. As illustrated, this sequence of four pulses are sufficient to provide each of the PI, AM, and AMPI signals. Because two half amplitude echo signals E1($o$), E1($e$) due to pulses P1($o$) and P2($e$) are produced, there is no need to double the received half amplitude signals via the +2 gain amplifier 112 as in the examples of FIGS. 1B and 1C.

The use of four pulses to provide each of the PI, AM, and AMPI signals reduces the time required to acquire the three sets of signals compared to acquiring PI, AM, and AMPI independently, but does not necessarily improve the efficacy of reducing the amount of non-perfused tissue contained in the corresponding images, especially in the presence of tissue motion.

SUMMARY OF THE INVENTION

It would be advantageous to provide a system and method that improves the quality of contrast-enhanced ultrasonic images by reducing the amount of non-perfused tissue (subsequently referred to as "tissue clutter") that appears in the ultrasound images, particularly tissue artifacts caused by tissue motion.

To better address one or more of these concerns, in an embodiment of this invention, a particular sequence of ultrasound transmissions and corresponding echo receptions enable the production of AM and AMPI signals that are temporally balanced. Temporal balancing significantly reduces tissue artifacts caused by movement of tissue during acquisition of the ultrasound echoes. Additionally, in combining the selected echo signals to produce the PI, AM, and AMPI signals, each of the echo signals is equally weighted to facilitate an amplitude balance that can produce ideal AM, and AMPI summations.

In an example embodiment, the sequence of transmit pulses comprises: (+0.5o, +1, +0.5e, −1, +0.5o), wherein the +/− sign indicates the phase of the transmission, the numerals indicate the amplitude, wherein o/e indicates complementary half aperture transmissions.

To produce the PI signal the second (+1) and fourth (−1) echoes are summed.

To produce a temporally balanced AM signal, the second echo (+1) is subtracted from the sum of the first (+0.5o) and third echoes (+0.5e).

To produce a temporally balanced AMPI signal, the third (+0.5e), fourth (−1), and fifth (−0.5o) signals are summed.

Images based on these PI, AM, and AMPI signals, individually or in combination, are displayed to a user. The combinations may be based on the signal-to-noise ratio (SNR) of one or more of the signals, as well as the spectral response of one or more of the signals, to further enhance the display of blood flow and blood perfusion in the patient.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

As detailed above, the prior art systems that employ PI, AM, and AMPI sub-modes for distinguishing tissue from blood flow and blood perfusion rely on the transmission of a sequence of pulses that are in some way complementary such that certain combinations of the echo signals from these pulses result in a cancellation of the linear echo signals from a stationary object (tissue), while preserving the non-linear signals due emanating from microbubbles in vessels or perfused tissue. These sub-modes (PI, AM, and AMPI) are premised on the assumption that the echoes from the stationary object are consistent throughout the duration of the sequence of pulses.

However, it is known that routine anatomic processes, such as the respiration cycle, cardiac cycle, and so on, as well as small movements introduced by the operator holding the ultrasound transducer will often cause the (relatively) stationary object to move. In some situations, such movement can be minimized, for example by asking the patient to hold his/her breath, but in other situations such motion is beyond the patient's control. This tissue motion introduces a non-linear component to the otherwise linear echo signals from stationary tissue. These non-linear echo signals are not cancelled-out by the conventional PI, AM, or AMPI sub-modes, which causes a partial appearance of a residual tissue component (clutter) in the ultrasound image ('motion-induced tissue artifacts). These artifacts diminish the clarity of the images documenting blood flow and tissue perfusion, and in some instances also diminish the diagnostic information that can be extracted from such images.

Heretofore, the particular order of pulses in the sequence has been considered irrelevant to the resultant ultrasound image ("the pulses in [an ultrasound] sequence can be transmitted in any order" (USPA 2005/0124895, which is incorporated by reference herein, [0021]); however, the inventors have determined that the order of the sequence of pulses in each sub-mode can have a significant effect on the magnitude of the appearance of motion-induced tissue artifacts. In the interest of ease of understanding, the examples provided herein are primarily directed to the AM and AMPI sub-modes, and one of skill in the art would recognize that the same principles could be applied to the PI sub-mode, as detailed further below. The reason that the order of pulses in an ultrasound transmission affects the magnitude of the motion-induced artifacts is illustrated in FIGS. 2A-2C, using the prior art pulse sequence of FIG. 1D.

Figure 2A:
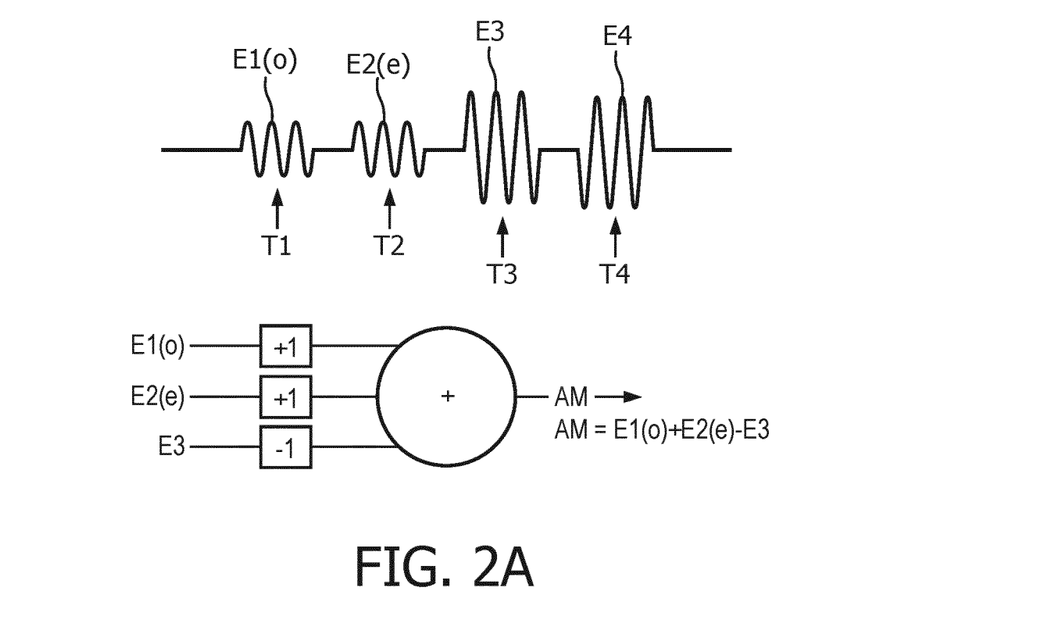
FIGS. 2A-2C illustrate the effects of tissue motion on a prior art sequence of ultrasound pulses.

FIG. 2A illustrates an example idealized reception of echo signals corresponding to the transmission of two half amplitude pulses (P1, P2 of FIG. 1D) followed by two full amplitude pulses (P3, P4), as these pulses are reflected from a stationary object at times T1, T2, T3, and T4. As illustrated, the AM signal from these echo signals amounts to E1(o)+E2(e)−E3. Ideally, in the absence of any non-linear echoes, this sum is zero; accordingly, any residual signal corresponds to non-linear echoes; which are primarily the microbubble echoes of interest.

Figure 2B:
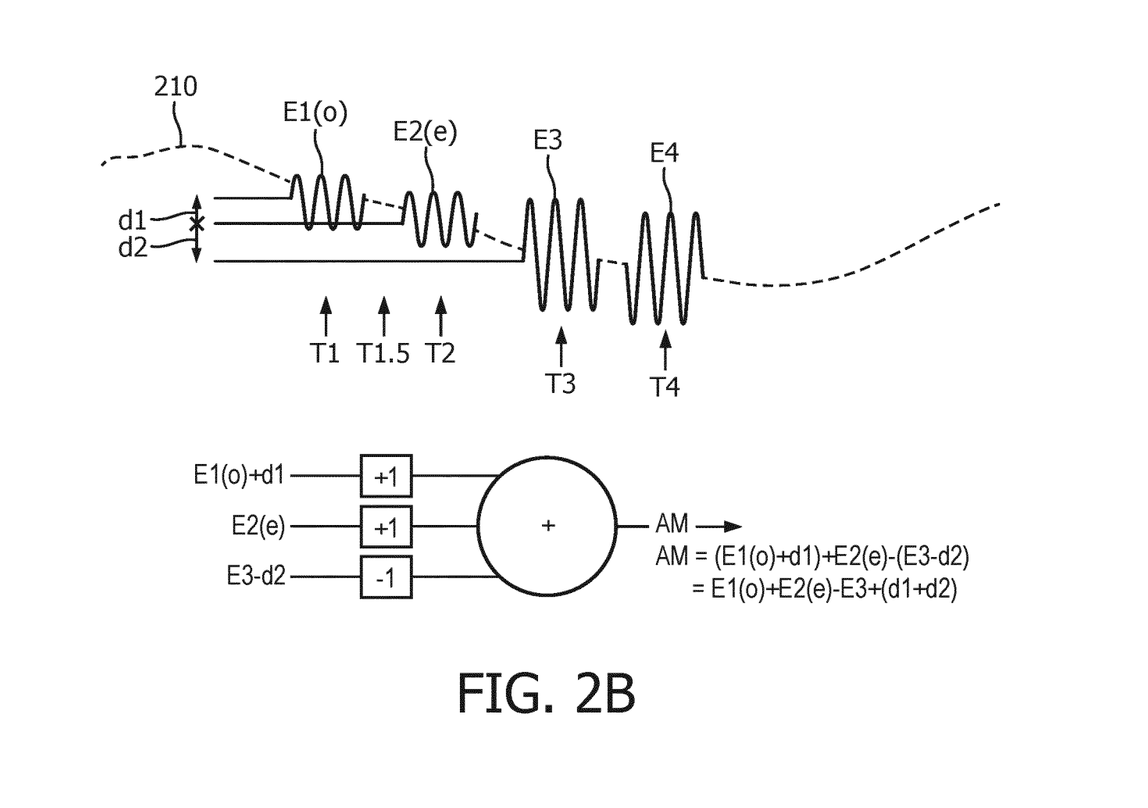
Figure 2C:
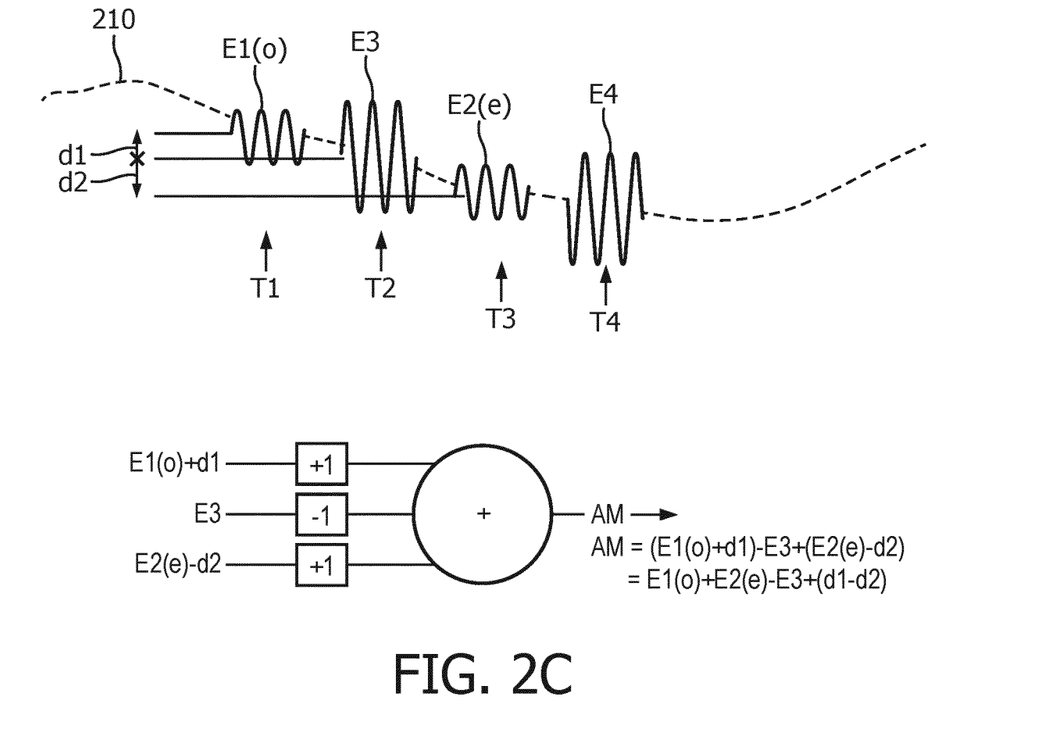

In FIG. 2B, tissue motion is illustrated by the dotted line 210. For illustrative effect, the echoes received at times T1, T2, T3, T4 are superimposed on the motion line 210. The echo signal E2($e$) differs from echo signal E1($o$) by a motion-induced difference d1, and echo signal E3 differs from echo signal E2($e$) by a motion-induced difference d2. Likewise, E4 will differ from E3. As noted above, the echoes are superimposed on the motion line 210 for illustrative effect. The differences d1 and d2 represent a difference in the received echo signals due to the motion of the tissue, which is assumed to be related to the distances that the tissue has moved. That is, when the tissue moves continuously in one direction, the echo signals are affected monotonically (i.e. continuously increase or continually decrease). The differences d1, d2 represent the parameters of the echo that are affected by the movement, not the distance that the tissue moves, per se. For ease of reference, these parameters are hereinafter referred to as the magnitude of the echo, and may refer to the magnitude of the amplitude of the echo, the magnitude of the frequency change of the echo, and so on, depending upon the technology used to process the echo signals. In like manner, the relative difference between the magnitudes of the echo signals may merely be referred to as being 'smaller' or 'larger'.

In this example, motion introduces a reduction in the received signal strength over the time period corresponding to the transmitted pulse sequence. Therefore, each subsequent echo is illustrated as being lower along the line of motion 210 relative to its preceding pulse. However, in other cases, each subsequent echo may be higher along the line of motion 210 relative to its preceding pulse.

In this simple illustrative example, relative to the center of the three echoes E1($o$), E2($e$), and E3 at T2, E1($o$) is larger than E2($e$) by an amount d1, and E3 is smaller than E2($e$) by an amount d2. Therefore, as illustrated in the summing arrangement of FIG. 2B, E1($o$)+d1, E2($e$), and E3−d2 will appear at their respective inputs. The resultant AM signal will therefore be (E1($o$)+E2($e$)−E3)+(d1+d2). The first term (E1($o$)+E2($e$)−E3) is the same as the AM signal in the absence of motion, as illustrated in FIG. 2A; therefore, the motion-induced effect on the AM signal amounts to (d1+d2) when the AM signal is produced by the P1($o$), P2($e$), P3 pulse sequence.

In like manner, the AMPI signal produced by the combination of E1($o$), E2(3), E4 will be offset by an even larger amount, because the difference between E2($e$) and E4 in this AMPI case is larger than the distance d2 between E2($e$) and E3 in the AM case, above.

Consider an alternative as illustrated in FIG. 2C, wherein the order of pulses to: P1($o$), P3, P2($e$), are changed with respect to FIG. 2B. This change produces echo signals E1($o$), E3, E2($e$), in that order. Using the same explanation as in FIG. 2B, relative to the center of these pulses along the line of motion 210 at T2, the received echo E1($o$) is larger than E3 by an amount d1, and the received echo E2($e$) is smaller than E3 by an amount d2. Correspondingly, the inputs to the summing arrangement will be expressed as E1($o$)+d1, E3, E2($e$)−d2. The output AM signal using this reordered sequence will therefore be (E1($o$)−E3+E2($e$))+(d1−d2). The term (E1($o$)−E3+E2($e$)) is equivalent to the AM signal in the absence of motion, as illustrated in FIG. 2A. Accordingly, the difference caused by motion using the sequence P1($o$), P3, P2($e$) is (d1−d2), as compared to the difference (d1+d2) caused by the same motion using the sequence P1($o$), P2($e$), P3.

It is significant to note that if the tissue motion has a relatively constant velocity, as is typical, for example, when the patient is inhaling or exhaling, the motion-induced differences d1 and d2 will be similar, and thus the difference (d1−d2) in the output AM signal due to motion using the sequence P1($o$), P3, P2($e$) will generally be substantially less than the differences (d1+d2) in the output AM signal due to motion using the prior art sequence P1($o$), P2($e$), P3. This substantial improvement in tissue cancellation is clearly evident in the images shown in FIGS. 5A, 5B, as detailed further below.

To explain which order of pulse sequences will be more or less effective in reducing motion-induced artifacts, the concept of "temporal balance" is introduced. As discussed above, the underlying principle behind tissue cancelation in contrast-enhanced ultrasound images is the use of two complementary sets of signals to cancel the echoes of each other as much as possible. With regard to motion-induced artifacts, the time that each pulse is transmitted, or the time that each echo is received, must be taken into account, because the magnitude of the echo signals vary with time, as detailed above with regard to FIGS. 2A-2C.

In FIG. 2C, using the pulse sequence P1($o$), P2, P3($e$), P4, and the combination E1($o$), E2, E2($e$) to provide the AM signal, the P1($o$) and P3($e$) signals form one complement, and the P2 signal forms the second complement. The motion-induced artifact of the AM signal is reduced compared to FIG. 2B because the echoes of the first complement (E1($o$), E2($e$)) occur on either side of the other complement (E3), providing a 'balanced' application of these complementary signals. Practically, this means that the summation of E1($o$) and E2($e$) produces a signal with a similar average displacement as E3. Contrarily, in FIG. 2B, both of the echoes of the first complement (E1($o$), E2($e$)) occur before the other complement (E3), so the effective displacement of the summed signals is different than E3.

In FIG. 2C, the time of occurrence of the complement echo (E3) is T2. The times of occurrences of the signals in the other complement echoes (E1($o$), E2($e$)) are T1 and T3. When the signals in the complement (E1($o$), E2($e$)) are combined, the time of occurrence of the entire complement of both signals is, effectively, their average time, T2. Because the effective time of occurrence of each of the sets of complementary signals is the same (i.e. at time T2), the set of signals E1($o$), E3, E2($e$) is said to be temporally balanced.

Conversely, in FIG. 2B, the signals of the first set of complement E1($o$), E2($e$) occur at times T1 and T2, with an effective time of occurrence of this set halfway between T1 and T2, which is designated T1.5 for convenience. The time of occurrence of the second set of complement E3 is at T3, which is distant from T1.5. Accordingly, the sequence E1($o$), E2($e$), E3 is said to be temporally unbalanced by 1.5 time units (T3−T1.5=1.5 time units). The greater the difference between the effective time of occurrence of each complement, the greater the magnitude of the motion-induced artifacts. For example, the AMPI signal produced by the combination of E1($o$), E2($e$), E4 of FIG. 2B has effective times of occurrences of each complement of T1.5 (the midpoint between E1($o$), E2($e$)) and T4, for a difference of 2.5 time units (T4−T1.5=2.5 time units). This confirms the statements above that the AMPI signal with effective times of T1.5 and T4 using the sequence P1($o$), P2($e$), P3, P4 will exhibit larger motion-induced artifacts than the AM signal that has effective times of T1.5 and T3 using that sequence.

However, the signals E1($o$), E2($e$), E4 of FIG. 2C that are used to produce the AMPI signal are also not temporally balanced. The temporal center of E1($o$) and E2($e$) is at T2, whereas the temporal center of E4 is at T4, which produces a temporal imbalance of 2 time units. This unbalance is less than the unbalance (2.5 time units) of the AMPI signal using the sequence in FIG. 2B, but still not sufficient to substantially reduce the motion-induced tissue artifacts in the AMPI signal.

It is significant to note that a four pulse sequence comprising two half-amplitude pulses and two full-amplitude pulses of opposite phase, as commonly used in prior art systems, cannot be arranged in any order to provide a temporal balance of both the AM and AMPI signals. It is also significant to note that a temporal balance of a PI signal using unity gain amplifiers requires at least four pulses comprising two at each phase, in order to create a temporal balance point between each pair of pulses at each phase. For example, a sequence of full pulses at {phase1, phase2, phase2, phase1) results in an effective time for the phase2 signals at the half-way point between the two pulses at phase2, which is also the effective time for the phase1 signals: half-way between the two pulses at phase1. Two consecutive full pulses in a sequence (i.e. phase2 in the above sequence) rarely, if ever, occur in prior art systems because redundant transmissions would conventionally be considered inefficient.

Figure 3:
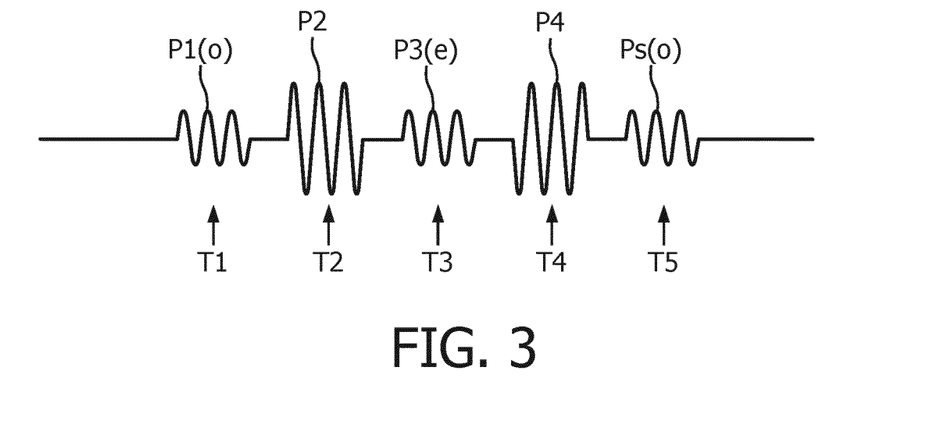
FIG. 3 illustrates a sequence of ultrasound pulses that enables the production AM and AMPI signals with reduced motion-induced artifacts, and PI signals.

FIG. 3 illustrates an example five pulse sequence that provides temporal balance for both AM and AMPI signals, and enables production of PI signals according to standard practice to those skilled in the art. This sequence is formed with three half-amplitude pulses P1($o$), P3($e$), P5($o$) separated from each other by two full-amplitude pulses P2 and P4. P2 and P4 have a phase opposite to each other while P1($o$), P3($e$), P5($o$) are in phase with each other and with P2. In an equivalent embodiment, P1($o$), P3($e$), and P5($o$) could be in phase with P1. For ease of illustration and understanding, the follow symbols are hereinafter defined. "o"=half-amplitude odd; "e"=half-amplitude even; "+"=full amplitude, phase 1; and "−"=full amplitude, phase 2. Accordingly, the sequence of FIG. 3 can be referred to as sequence (o, +, e, −, o), and the prior art sequence of FIG. 1D as sequence (o, e, +, −).

Figure 4A:
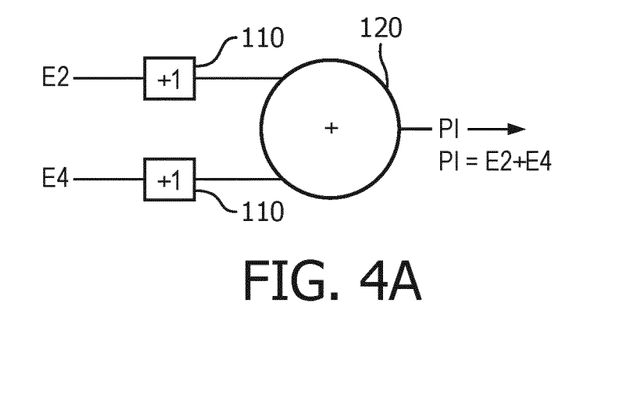
FIGS. 4A-4C illustrate a combination of echo processors that provide the AM and AMPI signals with reduced motion-induced artifacts, and the PI signals from the echoes of the sequence of FIG. 3.
Figure 4B:
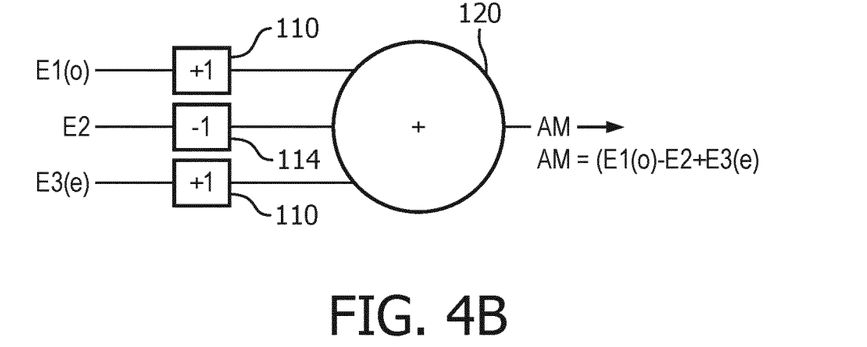
Figure 4C:
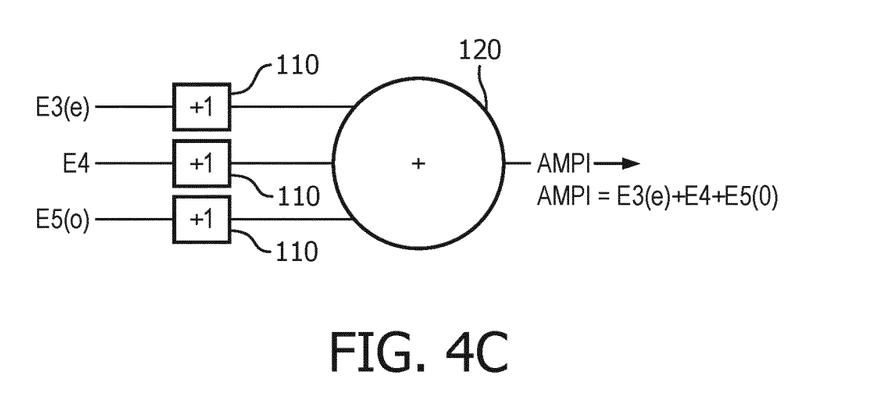

FIGS. 4A-4C illustrate the echo combining units for providing PI, AM, and AMPI ultrasound signals using unity-gain amplifiers 110, 114 and summers 120.

FIG. 4A illustrates the configuration for providing a PI signal based on the sum of full-amplitude, opposite phase, signals E2 and E4. As noted above, the balance of the PI signal is not addressed with respect to this example; the temporal imbalance of the PI signal is two time-units (T2-T4) i.e. the center of signal E2 is T2 and the center of signal E4 is T4.

FIG. 4B illustrates the configuration for providing an AM signal based on the sum of two half-amplitude echoes E1($o$), E3($e$) and a negative full-amplitude echo −E2. The effective time of occurrence of the set E1 ($o$), E3 ($e$) is T2 (the signals E1($o$) and E3 ($e$) are evenly displaced around a center point T2), and the effective time of occurrence of E2 is also T2 (the center of E2 is time T2), thus providing a temporally balanced AM signal.

FIG. 4C illustrates the configuration for providing an AMPI signal based on the sum of two half-amplitude echoes E3($e$), E5($o$) and a full-amplitude echo of opposite phase E4. The effective time of occurrence of the set E3($e$) and E5($o$) is T4 (the signals E3($e$) and E5($o$) are evenly displaced around a center point T4), and the effective time of occurrence of E4 is also T4 (the center of E4 is time T4), thus providing a temporally balanced AMPI signal.

As noted above, if the tissue motion is at a constant velocity, and the pulses are equally spaced, this sequence will substantially reduce motion-induced tissue artifacts in the AM and AMPI based images.

The PI signal is temporally unbalanced (T2, T4; unbalance of 2 time units), and will exhibit motion-induced artifacts. In embodiments of this invention, the AM or AMPI images, or both, may be compared to the PI images or combined with the PI images to identify and reduce motion-induced tissue artifacts from the PI images.

FIGS. 5A-5D illustrate the substantial improvement that can be achieved in ultrasound imaging by providing temporally balanced pulse sequences to produce temporally balanced AM and AMPI signals.

Figure 5A:
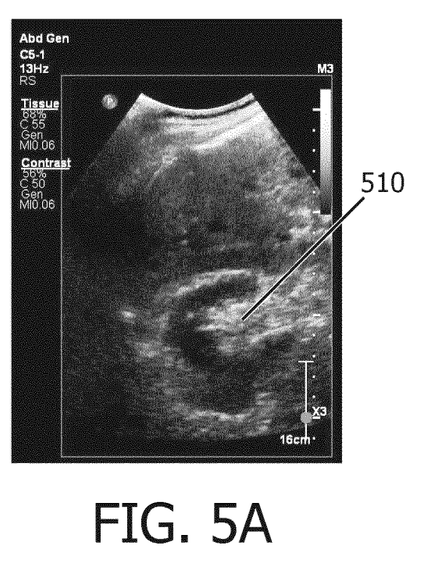
FIGS. 5A-5D illustrate ultrasound images with and without AM and AMPI temporally balanced echo signals.

FIG. 5A illustrates an ultrasound image obtained by the prior art transmission sequence of (o, e, +, −) (FIG. 1D), and using the o, e, and + echo signals to provide an AM signal (FIG. 1D).

Figure 5B:
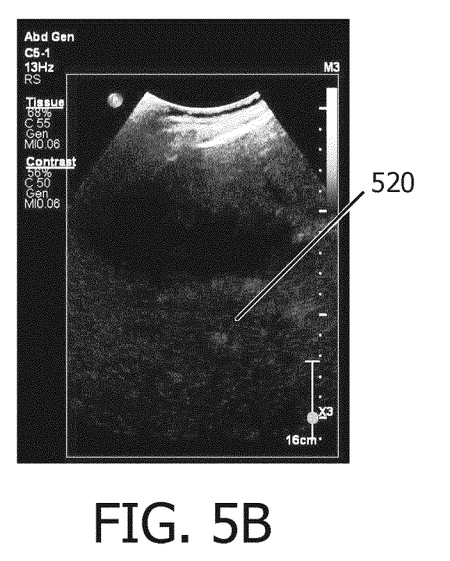

FIG. 5B illustrates an ultrasound image obtained by the example sequence of this invention: (o, +, e, −, o), and using the first three echo signals (o, +, e) to provide a temporally balanced AM signal (FIG. 4B).

A comparison of FIGS. 5A and 5B shows an example improvement at region 520 in FIG. 5B compared to region 510 in FIG. 5A. As can be seen, the ultrasound image of FIG. 5A produced using the prior art sequence of (o, e, +, −) introduces substantial "tissue clutter" at 510, due primarily to movement of the tissue during the acquisition of the echo signals (motion-induced tissue artifacts). By providing a transmission sequence (o, +, e, −, o) that enables reduction or elimination of motion-induced tissue artifacts by providing temporally balanced echo signals (o, +, e) in accordance with this invention, the region 520 exhibits substantially less tissue clutter compared to the region 510.

Figure 5C:
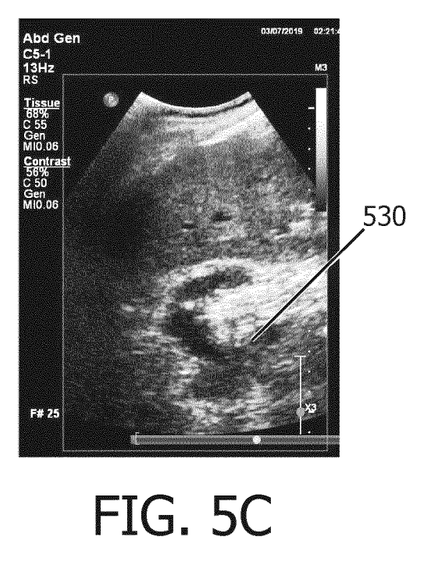

FIG. 5C illustrates an ultrasound image obtained by the prior art transmission sequence of (o, e, +, −), and using the o, e, and − echo signals to provide an AMPI signal (FIG. 1D). As can be seen, and as discussed above, because of the larger temporal unbalance (T1.5-T4) of the echo signals used to produce the AMPI image of FIG. 5C compared to the temporal unbalance (T1.5-T3) of the echo signals used to produce the AM image of FIG. 5A, the degree of tissue clutter at region 530 in the AMPI image of FIG. 5C is recognizably greater than the tissue clutter at region 510 produced in the AM image of FIG. 5A.

Figure 5D:
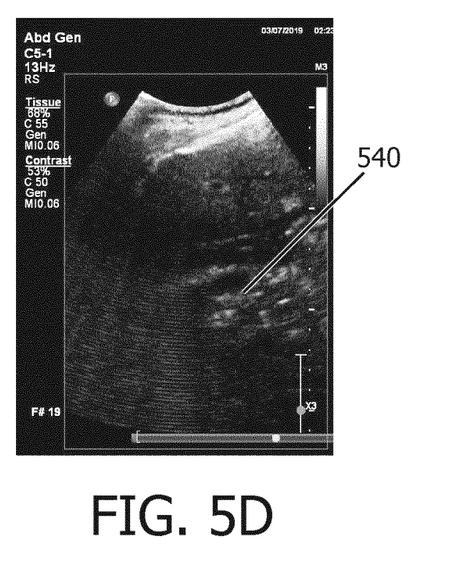

FIG. 5D illustrates an ultrasound image obtained by the example sequence of this invention (o, +, e, −, o) and using the last three e, −, and o echo signals to provide a temporally balanced AMPI signal. As can be seen, the amount of tissue clutter at 540 in FIG. 5D is substantially less than the amount of tissue clutter at 530 in FIG. 5C.

Figure 6:
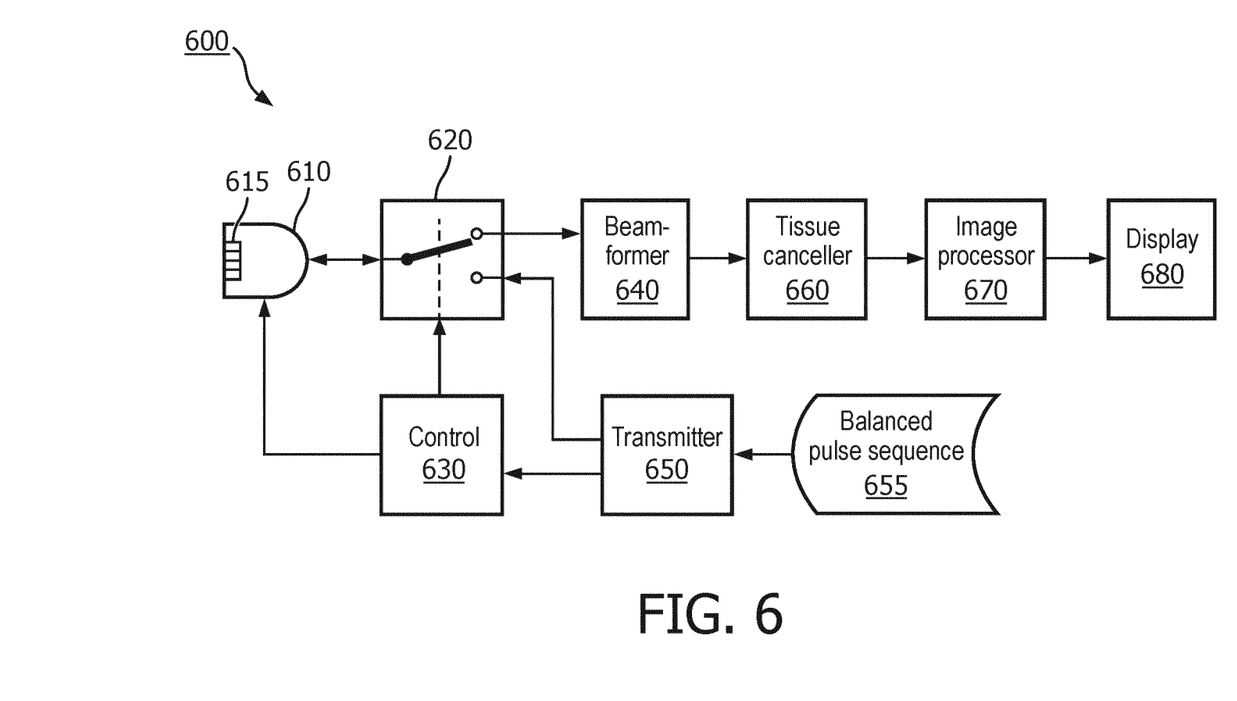
FIG. 6 illustrates an example block diagram of an ultrasound system.

FIG. 6 illustrates an example block diagram of an ultrasound system 600 in accordance with an aspect of this invention.

A scanhead 610 includes a plurality of transducer elements 615 and a controller 630. The plurality of transducer elements 615 transmit and receive ultrasound signals. The controller 630 determines whether signals are provided to the transducer elements for transmission or signals are received from the transducer elements, via a switch 620. The transducer elements are typically configured as a matrix, with each transducer being sequentially numbered; in this manner, the transducer elements can provide half-amplitude signals by enabling either the odd or even numbered transducer elements as described above.

When the switch 620 is in the transmit state, the transmitter 650 provides a sequence of temporally balanced pulses 655 to the transducer elements. The transmitter 650 also notifies the controller 630 which set of transducer elements (all, odd, even) should be enabled for each pulse in the sequence, and the controller 630 controls the transducer elements 615 accordingly.

In the receive mode, the received echoes are directed to the beam former 640 by the switch 620, then processed by the tissue canceller 660 to provide PI, AM, and AMPI signals. The echo signals are processed in the canceller 660 in the conventional manner, except that, because the transmitted pulses are temporally balanced, the results of the processing of the echoes for tissue cancellation via the AM or AMPI sub-mode at the canceller 660 will be substantially improved compared to the results of AM or AMPI processing of non-temporally balanced echoes.

The resultant PI, AM, and AMPI signals from the tissue canceller 660 are provided to an image processor that selectively creates images based on each of the PI, AM, and AMPI signals, or a combination of two or more of these signals. As noted above, each of these tissue-canceled PI, AM, and AMPI sub-modes has particular advantages and disadvantages. For example, each sub-mode PI, AM, and AMPI contains a unique frequency-dependent response from the microbubbles and tissue. Accordingly, in some embodiments a blending at each pixel, or each region can be determined by the strongest properties over several frequency bands. In some embodiments, the regions and frequency bands of each sub-mode containing highest microbubble signal-to-noise may be used to blend the pixels into a final image.

As noted above, the sub-mode data could be used to identify regions of tissue clutter in particular images, and the images could be masked or blended to suppresses unwanted tissue artifacts.

In like manner, changes in the bubble spectral response over depth/time could be used to change the proportion of blending, in situations where one sub-mode is dominant in an arterial phase and another sub-mode in a later phase. That is, for example, the AM output signal may exhibit less clutter during the arterial phase, and the AMPI output may exhibit less clutter during the portal venous phase, and a composite image may be formed by selectively blending the AM and AMPI outputs based on phase.

The images produced by the image processor 670 are communicated to a display device 680. At the display, a variety of combinations of images can be displayed, including for example, displaying the images of each sub-mode PI, AM, and AMPI simultaneously to the clinician so that the different information contained in each sub-mode can be assessed. In like manner, images based on combinations of the sub-mode signals may be selectively displayed, with or without a simultaneous display of the underlying sub-mode images.

Figure 7:
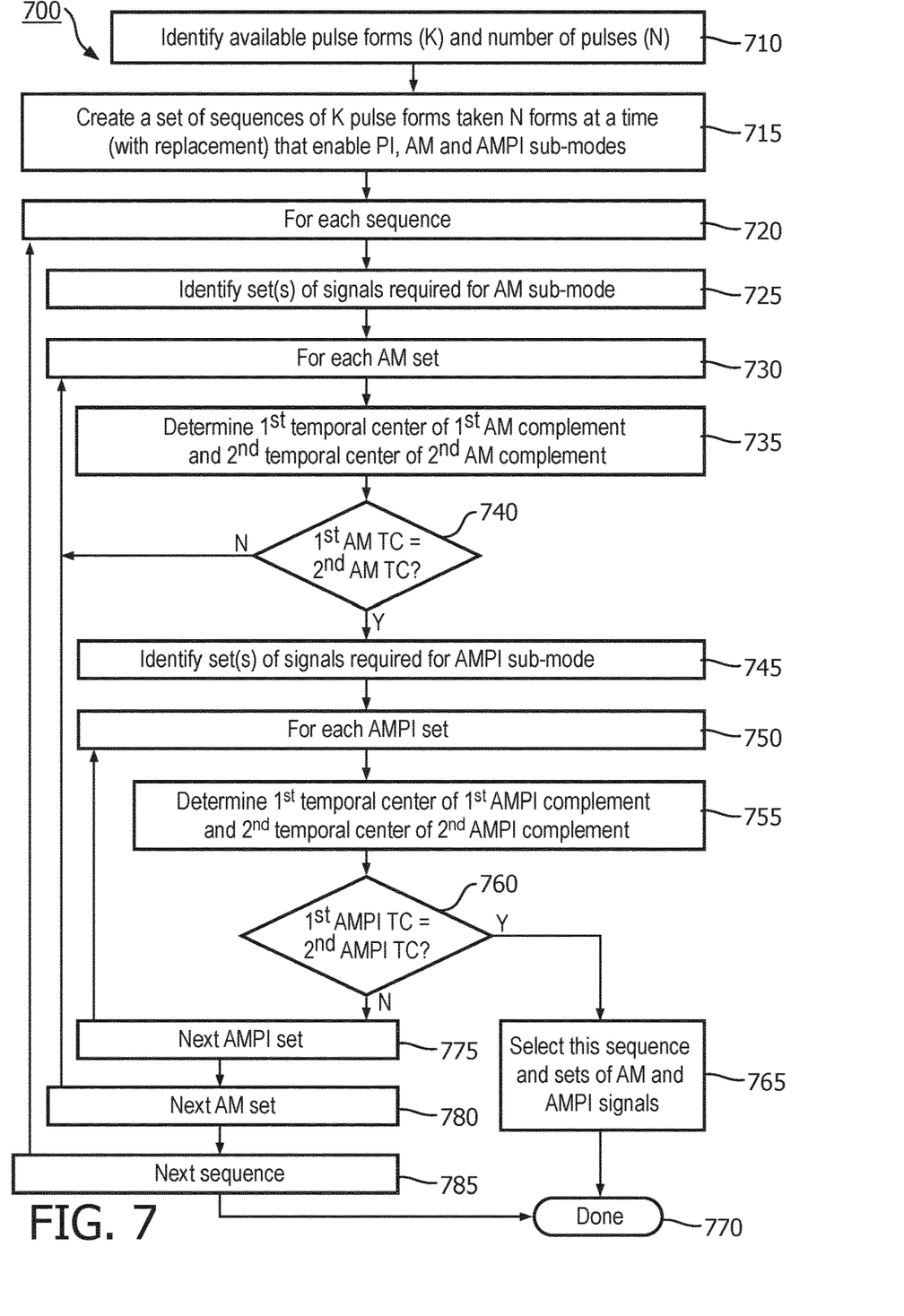
FIG. 7 illustrates an example flow diagram for creating a pulse sequence that produces temporally balanced AM and AMPI signals.

As noted above, the pulse sequence of FIG. 3 is only an example of a pulse sequence that provides temporally balanced AM and AMPI signals. FIG. 7 illustrates an example flow diagram 700 for producing a temporally balanced ultrasound pulse sequence(s) limited by a fixed number of pulses in the sequence. The sequence provides temporally balanced AM and AMPI signals, and, as detailed further below, may be extended to also provide temporally balanced PI signals. One of skill in the art will recognize that alternative processes may be used as well.

At 710 the number of different pulse forms (e.g. half-odd, half-even, full-phase1, full-phase2, or others) that are available for transmission are identified, and the number of pulses forming the sequence (typically five or more) is selected. Based on the available pulse forms and the number of pulses forming the pulse sequence, the possible sequences of these K pulse forms taken N at a time, with duplication, are determined, and filtered to eliminate any pulse sequence that does not enable PI, AM, and AMPI sub-modes (such as all pulses of the same phase, no half-amplitude pulses, etc.), at 715.

The loop 720-785 processes each feasible sequence to determine whether a temporally balanced AM signal and a temporally balanced AMPI signal can be formed from this sequence.

At 720 the loop begins and incrementally tests each of the potential sequences identified at 715, until a temporally balanced sequence is found (at 765). Alternatively, all of the potential sequences may be tested to create a set of temporally balanced sequences. The sequences in this set may be assessed to select a preferred sequence, based on some other criteria, such as where in the sequence the temporal balance points lie.

At 725, the set(s) of signals in the sequence that can be used to provide an AM signal are identified. The sequence may contain alternative arrangements (sets) of echoes to provide an AM signal. In the loop 730-780, each of the sets of echoes are processed to determine if the set is temporally balanced. At 730, the loop starts and incrementally selects each set of potential sequences for producing the AM signal identified at 725. At 735, the temporal centers of each of the sets of complementary signals (e.g. (half-odd, half-even), (full-phase1)) are determined, and compared at 740. If this set of signals in the sequence cannot provide an AM temporal balance ('No' at 740), the set is unsuitable, and the next AM set, if any, is processed.

If, at 740, the sequence provides a temporally balanced AM signal, the sets of signals in the sequence that provide an AMPI signal are identified, at 745, and the loop 750-775 determines whether each AMPI set also provides a temporally balanced AMPI signal. The temporal centers of the complementary sets of signals (e.g. (half-odd, half-even), (full-phase2)) are determined at 755, and compared at 760. If the temporal centers are the same, this sequence is suitable for providing both the temporally balanced AM signal and the temporally balanced AMPI signal, and this sequence and the sets of AM and AMPI pulse signals are selected, at 765.

Having found a pulse sequence that provides temporally balanced AM and AMPI signals, further processing is unnecessary, and the process is terminated at 770. Due to the fact that the possible sequences at 715 must be able to provide a PI signal, this selected sequence is assured to also provide a PI signal.

If the set of signals cannot provide a temporally balanced AMPI signal, at 760, the next AMPI set, if any, is processed in the loop 750-775. After the all of the AMPI sets for this sequence are determined not to provide a temporally balanced AMPI signal, the next set of AM signals, if any, are processed in the loop 730-780. If the sequence is not able to provide temporally balanced AM and AMPI signals, the next sequence is assessed in the loop 720-785. If no sequence can be found to provide temporally balanced AM and AMPI signals, the process is terminated without selecting a sequence, at 770.

One of skill in the art will recognize that the flow diagram of FIG. 7 may be modified to find a sequence that provides temporally balanced PI, AM, and AMPI signals.

If the sequence provides AM balance at 740, and AMPI balance at 760, the process could be modified to subsequently determine if this sequence can also provide a balanced PI signal, using the same technique of identifying the sets of pulses that can be used to provide the PI signal, then assessing whether one of the sets provides a temporally balance PI signal. For example, by increasing N, from five pulses in the sequence to eight pulses, the modified process will identify a sequence (o, +, e, −, o, −e, +) that will provide temporally balanced PI, AM, and AMPI signals. The PI signal {+}, {−}, {−}, {+} from the $2^{nd}$, $4^{th}$, $6^{th}$, and $8^{th}$ pulses is balanced at T5; the AM signal {o}, {+}, {e} from the $1^{st}$, $2^{nd}$ and $3^{rd}$ pulse is balanced at T2; and the AMPI signal {e}, {−}, {o} from the $3^{rd}$, $4^{th}$ and $5^{th}$ pulse is balanced at T4. Optionally, another AMPI signal {o}, {−}, {e} may be obtained from the $5^{th}$, $6^{th}$ and $7^{th}$ pulses, balanced at T6.

Although an increase in the size of the sequence consumes more time per sample, in certain situations, the reduction or elimination of motion-induced artifacts in each of the sub-modes may be worth the extra time. Additionally, because the AMPI signal can be provided by the e, o signals (T4) or the o, −, e signals (T6), both signals may be produced and combined to potentially provide an improved AMPI signal.

One of skill in the art will recognize that the flow diagram of FIG. 7 may also be used to provide different temporally balanced signals. For example, replacing "AMPI" in the blocks of FIG. 7 with "PI" will produce a sequence that provides temporally balanced AM and PI signals; replacing "AM" with "PI" in FIG. 7 will produce a sequence that provides temporally balanced PI and AMPI signals. In like manner, if the temporally unbalance signal (e.g. PI) is not expected to be used, the test at block 725 can omit the requirement that the sequence is able to produce this temporally unbalanced signal.

One of skill in the art will also recognize that the principles of this invention may be applied to any set of signals that are subject to motion-induced artifacts and use complementary sets of signals to cancel an underlying unwanted signal. That is, the flow diagram of FIG. 7, and the example extensions, may be applied if different sub-modes and/or different pulse types are found to cancel the underlying unwanted signal.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein the order of the sequence is reversed, the phases are reversed, and so on, provided that the resultant sequence remains temporally balanced. That is, for the purposes of understanding this invention as disclosed in the claims, the use of the terms 'positive' and 'negative', 'odd' and 'even', are not absolute, but are relative to each other.

Figure 8:
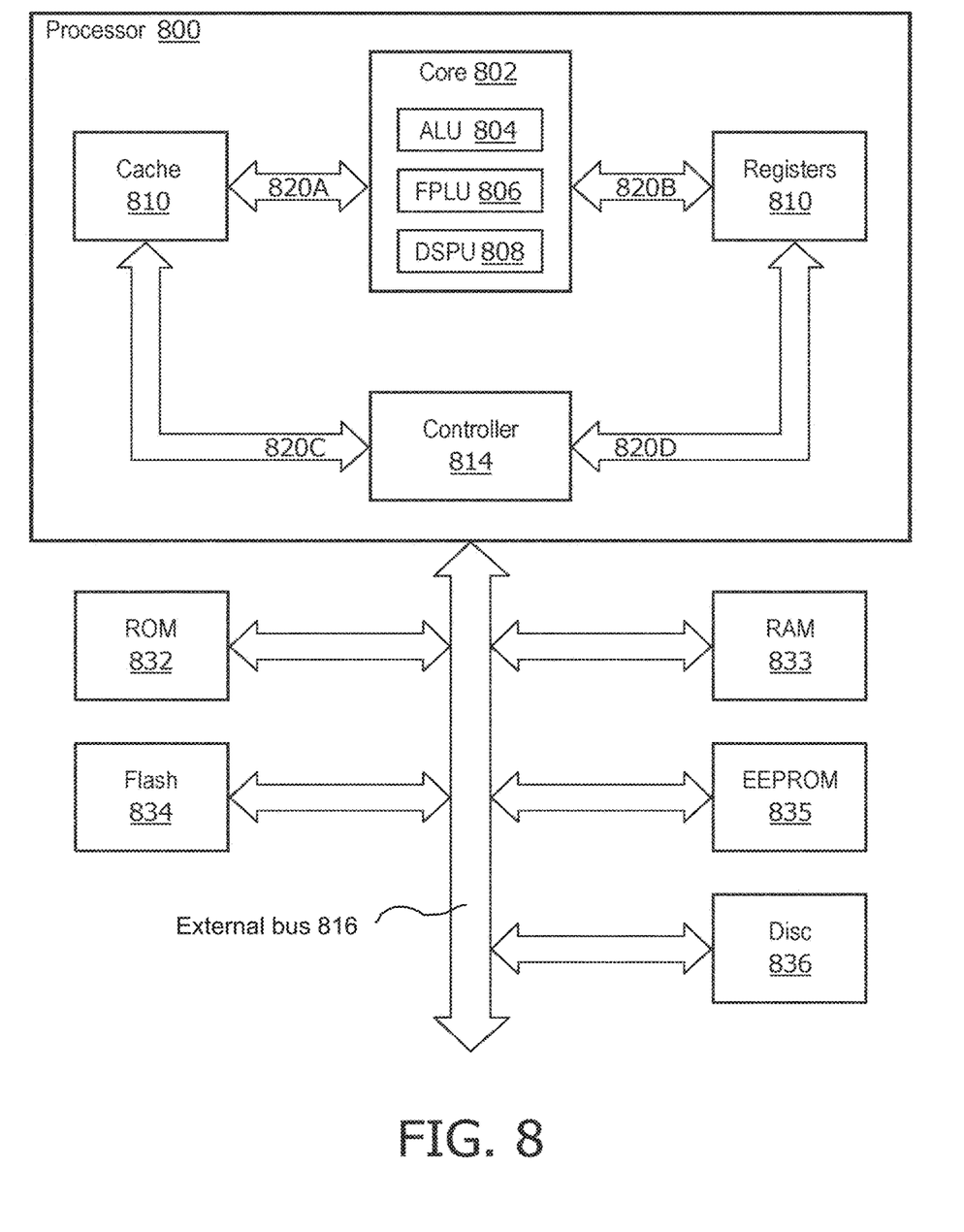
FIG. 8 illustrates a block diagram showing an example processor according to embodiments of the invention.

FIG. 8 is a block diagram illustrating an example processor 800 according to embodiments of the disclosure. Processor 800 may be used to implement one or more processors described herein, for example, any or all of the processing elements shown in FIG. 6. Processor 800 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 800 may include one or more cores 802. The core 802 may include one or more arithmetic logic units (ALU) 804. In some embodiments, the core 802 may include a floating point logic unit (FPLU) 806 and/or a digital signal processing unit (DSPU) 808 in addition to or instead of the ALU 804.

The processor 800 may include one or more registers 812 communicatively coupled to the core 802. The registers 812 may be implemented using dedicated logic gate circuits (e.g., flip-flops) and/or any memory technology. In some embodiments the registers 812 may be implemented using static memory. The register may provide data, instructions and addresses to the core 802.

In some embodiments, processor 800 may include one or more levels of cache memory 810 communicatively coupled to the core 802. The cache memory 810 may provide computer-readable instructions to the core 802 for execution. The cache memory 810 may provide data for processing by the core 802. In some embodiments, the computer-readable instructions may have been provided to the cache memory 810 by a local memory, for example, local memory attached to the external bus 816. The cache memory 810 may be implemented with any suitable cache memory type, for example, metal-oxide semiconductor (MOS) memory such as static random access memory (SRAM), dynamic random access memory (DRAM), and/or any other suitable memory technology.

The processor 800 may include a controller 814, which may control input to the processor 800 from other processors and/or components included in a system (e.g., component BBB shown in FIG. B) and/or outputs from the processor 800 to other processors and/or components included in the system (e.g., component CCC shown in FIG. C). Controller 814 may control the data paths in the ALU 804, FPLU 806 and/or DSPU 808. Controller 814 may be implemented as one or more state machines, data paths and/or dedicated control logic. The gates of controller 814 may be implemented as standalone gates, FPGA, ASIC or any other suitable technology.

The registers 812 and the cache 810 may communicate with controller 814 and core 802 via internal connections 820A, 820B, 820C and 820D. Internal connections may be implemented as a bus, multiplexor, crossbar switch, and/or any other suitable connection technology.

Inputs and outputs for the processor 800 may be provided via a bus 816, which may include one or more conductive lines. The bus 816 may be communicatively coupled to one or more components of processor 800, for example the controller 814, cache 810, and/or register 812. The bus 816 may be coupled to one or more components of the system, such as components BBB and CCC mentioned previously.

The bus 816 may be coupled to one or more external memories. The external memories may include Read Only Memory (ROM) 832. ROM 832 may be a masked ROM, Electronically Programmable Read Only Memory (EPROM) or any other suitable technology. The external memory may include Random Access Memory (RAM) 833. RAM 833 may be a static RAM, battery backed up static RAM, Dynamic RAM (DRAM) or any other suitable technology. The external memory may include Electrically Erasable Programmable Read Only Memory (EEPROM) 835. The external memory may include Flash memory 834. The External memory may include a magnetic storage device such as disc 836. In some embodiments, the external memories may be included in a system, such as ultrasound imaging system 600 shown in FIG. 6.

Although the processor 800 is shown as distinct from the external bus 816 and memories 832, 834, 833, 835 and disc 836 some or all of these items may be part of the "processor" 800 in alternative embodiments. It should be understood that the term processor, processor system, computer, computer system controller or controller system may refer to the processor 800 alone or to the processor along with some or all of the elements 816, 832, 834, 833, 835 and 836.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Reference numerals and symbols that appear in the claim are for ease of understanding only, and represent example embodiments; they are not intended to limit the scope of the claims. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound method for distinguishing non-perfused tissue from at least one of blood flow or blood perfusion comprising:
   transmitting a sequence of ultrasound signals including a first complement and a second complement to a patient via a plurality of ultrasound transducer elements;
   receiving a sequence of echo signals corresponding to the sequence of ultrasound signals;
   combining a first selected set of echo signals to produce an Amplitude Modulated (AM) signal;
   combining a second selected set of echo signals to produce an Amplitude Modulated Phase Inversion (AMPI) signal;
   creating at least one image based on at least one of the AM signal or the AMPI signal;
   displaying the at least one image;
   wherein at least one of an order of at least one of the first selected set of echo signals or the second selected set of echo signals is temporally balanced by having echo signals of the first complement in the first selected set or the second selected set occur on each side of an echo signal of the second complement in the first selected set or the second selected set, or center times of the first selected set of echo signals or the second selected set of echo signals are temporally balanced by having center times of echo signals of the first complement in the first selected set or the second selected set evenly displaced around a center time of an echo signal of the second complement in the first selected set or the second selected set;
   wherein a characteristic of each of the echo signals is set to be equal in each combining to produce the AM and AMPI signals.

2. The method of claim 1,
   wherein the sequence of ultrasound signals comprises a sequence of a first signal, a second signal, a third signal, a fourth signal, and a fifth signal;
   wherein the first signal and the fifth signal correspond to a transmission through a first half of the plurality of ultrasound transducer elements at a first phase;
   wherein the second signal corresponds to a transmission through the plurality of transducer elements at the first phase;
   wherein the third signal corresponds to a transmission through a second half of the plurality of ultrasound transducer elements at the first phase; and
   wherein the fourth signal corresponds to a transmission through the plurality of transducer elements at a second phase.

3. The method of claim 2,
   wherein the first signal corresponds to a first echo signal,
   wherein the second signal corresponds to a second echo signal,
   wherein the third signal corresponds to a third echo signal.

4. The method of claim 2, wherein the AMPI signal comprises a sum of the third signal, the fourth signal, and the fifth signal.

5. The method of claim 2, wherein the method comprises summing the second signal and the fourth signal to provide a Phase Inverted (PI) signal, and wherein the at least one image is also based on the PI signal.

6. The method of claim 1, wherein the AMPI signal produced by combining the second selected set of echo signals is temporally balanced.

7. The method of claim 1, wherein the at least one image is further based on a spectral response of at least one of the AM signal or the AMPI signal.

8. The method of claim 1, wherein the at least one image is further based on a signal-to-noise ratio of at least one of the AM signal or the AMPI signal.

9. The method of claim 1, wherein the at least one image comprises at least two images, and wherein the method comprises simultaneously displaying the at least two images.

10. The method of claim 1, wherein the at least one image comprises a combination image that is based on both the AM and AMPI signals.

11. The method of claim 1,
    wherein each of the selected first set of echo signals and the selected second set of echo signals comprises a first set of echo signals and a second set of echo signals;
    wherein a form of the first set of echo signals and the second set of echo signals are complementary;
    wherein the first set of echo signals has a first center time;
    wherein the second set of echo signals has a second center time; and
    wherein the first center time is equal to the second center time.

12. The method of claim 1, further comprising injecting contrast-enhancing microbubbles in a vessel of the patient; wherein the at least one image displays a flow of the microbubbles through the patient.

13. An ultrasound system, comprising:
    a plurality of transducer elements configured to transmit a sequence of ultrasound pulses and to receive a sequence of echo signals in response to the sequence of ultrasound pulses; and
    a processing circuit configured to generate the sequence of ultrasound pulses and to process the sequence of echo signals as claimed in claim 1.

14. A non-transitory computer-readable medium that includes a program that, when executed by a processing system, causes the processing system to:
    transmit a sequence of ultrasound signals including a first complement and a second complement to a patient via a plurality of ultrasound transducer elements;
    receive a sequence of echo signals corresponding to the sequence of ultrasound signals;
    combine a first selected set of echo signals to produce an Amplitude Modulated (AM) signal;

combine a second selected set of echo signals to produce an Amplitude Modulated Phase Inversion (AMPI) signal;

create at least one image based on at least one of the AM signal or the AMPI signal;

display the at least one image;

wherein at least one of an order of each of the first selected set of echo signals and the second selected set of echo signals is temporally balanced by having echo signals of the first complement in the first selected set or the second selected set occur on each side of an echo signal of the second complement in the first selected set or the second selected set, or center times of the first selected set of echo signals and the second selected set of echo signals are temporally balanced by having center times of echo signals of the first complement in the first selected set or the second selected set evenly displaced around a center time of an echo signal of the second complement in the first selected set or the second selected set;

wherein a characteristic of each of the echo signals is set to be equal in each combining to produce the AM and AMPI signals; and wherein the at least one image minimizes an appearance of motion-induced tissue artifacts in the images.

15. The medium of claim 14, wherein:

the sequence of ultrasound signals comprises a sequence of a first signal, a second signal, a third signal, a fourth signal, and a fifth signal;

the first signal and the fifth signal correspond to a transmission through a first half of the plurality of ultrasound transducer elements at a first phase;

the second signal corresponds to a transmission through the plurality of transducer elements at the first phase;

the third signal corresponds to a transmission through a second half of the plurality of ultrasound transducer elements at the first phase; and the fourth signal corresponds to a transmission through the plurality of transducer elements at a second phase.

* * * * *